United States Patent [19]

Kami et al.

[11] Patent Number: 5,558,619

[45] Date of Patent: Sep. 24, 1996

[54] ENDOSCOPE SYSTEM WITH AUTOMATIC CONTROL ACCORDING TO MOVEMENT OF AN OPERATOR

[75] Inventors: Kuniaki Kami; Hideyuki Adachi, both of Hachioji; Kōichi Umeyama, Kasukabe; Yoshihiro Kosaka, Hachioji; Seiji Yamaguchi, Hachioji; Eiichi Fuse, Hachioji; Michio Sato, Hino; Masakazu Nakamura, Hachioji; Yasundo Tanaka, Urawa; Takashi Fukaya, Hachioji; Kiyotaka Matsuno, Hachioji; Katsuya Suzuki, Hachioji, all of Japan

[73] Assignee: Olympus Optical Co., Ltd., Tokyo, Japan

[21] Appl. No.: 306,726

[22] Filed: Sep. 15, 1994

Related U.S. Application Data

[63] Continuation of Ser. No. 863,869, Apr. 6, 1992, abandoned.

[30] Foreign Application Priority Data

Apr. 23, 1991 [JP] Japan .................. 3-092235

[51] Int. Cl.$^6$ .................................... A61B 1/00
[52] U.S. Cl. .......................... 600/146; 600/106; 600/921
[58] Field of Search ..................... 600/117, 118, 600/146, 106, 921; 348/45, 42, 65; 128/4, 6, 657; 358/98, 88, 104, 103; 273/438, 148.13; 356/1, 152; 340/706, 709; 395/135; 364/413.01, 413.13; 901/2, 6, 8

[56] References Cited

U.S. PATENT DOCUMENTS

| | | | |
|---|---|---|---|
| 4,103,435 | 8/1978 | Herndon | 358/104 X |
| 4,439,755 | 3/1984 | Larussa | 358/104 X |
| 4,601,705 | 7/1986 | McCoy | 128/4 X |
| 4,757,380 | 7/1988 | Smets et al. | 358/88 |
| 4,837,734 | 6/1989 | Ichikawa et al. | 901/2 X |
| 4,840,176 | 6/1989 | Ohno | 606/127 X |
| 4,930,888 | 6/1990 | Freisleben et al. | 358/104 X |
| 4,941,456 | 7/1990 | Wood et al. | 128/6 |
| 4,956,794 | 9/1990 | Zeevi et al. | 358/104 X |
| 4,984,179 | 1/1991 | Waldren | 358/104 X |
| 5,086,401 | 2/1992 | Glassman | 364/413.01 X |
| 5,091,779 | 2/1992 | Ams et al. | 358/98 |
| 5,171,233 | 12/1992 | Amplatz et al. | 606/113 X |
| 5,175,616 | 12/1992 | Milgram et al. | 358/88 |

FOREIGN PATENT DOCUMENTS

| | | | |
|---|---|---|---|
| 0239884 | 10/1986 | Germany | 364/413.01 |
| 0262613 | 10/1988 | Japan | 128/4 |

OTHER PUBLICATIONS

Fisher et al., "Virtual Environment Display System", Oct. 1986, pp. 1–10.

Pimentel et al., *Virtual Reality*, 1993, pp. 194–208 (Chapter 11).

*Primary Examiner*—Richard J. Apley
*Assistant Examiner*—John P. Leubecker
*Attorney, Agent, or Firm*—Armstrong, Westerman, Hattori, McLeland & Naughton

[57] ABSTRACT

An endoscope system includes a movement detector for detecting an operator's movement, a signal processor for processing a signal the detector detects, and a control for controlling drive which drives a medical device according to an output signal of the signal processor. The endoscope system bends a bending section of an endoscope serving as a medical device according to the operator's movement, and thus orients the observation field of view to a direction the operator intends or controls the movement of a treatment adapter serving as a medical device. The endoscope system includes a superimposing means for superimposing an image associated with the operator's movement onto an image acquired by an imaging device associated with the endoscope system.

10 Claims, 4 Drawing Sheets

ENDOSCOPE SYSTEM WITH AUTOMATIC CONTROL ACCORDING TO MOVEMENT OF AN OPERATOR

This application is a continuation of application Ser. No. 07/863,869 filed Apr. 6, 1992, now abandoned.

BACKGROUND OF THE INVENTION

1. Field of the Invention

The present invention relates to an endoscope system for simplifying endoscopic operations for observing or applying various treatments to intended regions.

2. Description of the Related Art

Endoscopes have been adopted widely in recent years, whereby an internal body cavity can be observed by inserting an elongated insertion tube or treated using a treatment adapter, if necessary.

When the endoscope is inserted into a tortuous body cavity or other insertion path, the bending section of the endoscope must be bent according to the tortuosity of the insertion path. To observe an intended object region with the endoscope inserted deeply to a body cavity, the bending section must be bent so that the field of view of an observation optical system formed at the distal end of an insertion tube must be directed to the object region.

In examples of prior art, an endoscope is automatically inserted into a tortuous path in a body cavity. The examples of prior art have been disclosed in Japanese Patent Laid-Open Nos. 3-109023, 3-92126, and 1-148232. Each example of the prior art comprises an insertion drive for automatically inserting the insertion tube of an endoscope into a duct, a bending drive for automatically bending a bending section formed at the distal end of the insertion tube of the endoscope, and a bending control in which when the insertion tube is inserted automatically into the duct, an observation system formed at the distal end of the insertion tube detects a dark area. Then the bending section is bent towards the dark area to orient the distal end of the insertion tube towards the center of the duct. According to the examples of the prior art, the insertion tube of the endoscope can be automatically inserted into tortuous ducts of body cavities. However, after the insertion tube is inserted into a duct, the bending section must be bent manually to orient the distal end of the endoscope towards an object region, so that the observation field of view will align with the object region. Moreover, a treatment adapter must be thrust manually from the distal end of the insertion tube, which has been placed in a duct of a body cavity, into the duct to perform various treatments.

On the other hand, Japanese Utility Model Laid-Open No. 2-55907 has described an endoscope bending unit. Herein, when the insertion tube of an endoscope is inserted into a duct of a body cavity, an observed image the distal end (observation system) of the insertion tube acquires is displayed on a monitor, the position of a view point of an operator who catches the monitor within his/her field of view is detected, then a bending section is bent according to the detected positional information of the view point. However, when the bending section is bent according to view point position information indicating an operator's view point within his/her field of view, every time the operator averts his/her view point to, for example, compare a certain point with another point while examining (observing) an object region, the bending section bends. Furthermore, the operator's view point must be set at a position to which the distal end of the endoscope is oriented, fatiguing the operator terribly.

OBJECTS AND SUMMARY OF THE INVENTION

The object of the present invention is to provide an endoscope system capable of automatically bending a bending section in association with a predefined operator's movement and orienting the distal end of an insertion tube of an endoscope to an object region of an operator's interest, so that the object region will coincide with the field of view of the endoscope placed in a duct of a body cavity.

Another object of the invention is to provide an endoscope system capable of automatically operating a treatment adapter in association with a predefined operator's movement to perform a treatment the operator intends.

Another object of the invention is to provide an endoscope system for resolving such drawbacks of the aforesaid view point detection mode of prior art that when an operator averts his/her view point during examination (observation), the field of view of an endoscope changes (the bending section bends) or that an operator fatigues terribly.

Another object of the invention is to provide an endoscope system for allowing an operator to set the field of view of an endoscope at an intended object region effortlessly.

Another object of the invention is to provide an endoscope system for allowing an operator to operate a treatment adapter as he/she intends and thus perform an intended treatment effortlessly.

A medical system of the present invention comprises a medical device for applying medical care to a subject, a driving means for actuating the medical device, a movement detecting means for detecting a movement of an operator who operates the medical device, and a control means for controlling drive of the driving means so that the driving means will actuate the medical device according to an operator's movement the movement detecting means detects.

Other features and advantages of the present invention will be apparent with the description below.

BRIEF DESCRIPTION OF THE DRAWINGS

FIG. 1 is an explanatory configuration diagram;

FIG. 2 is an explanatory diagram showing a detector for detecting the positional state of a head;

FIGS. 3 to 7 relate to the second embodiment;

FIG. 3 is a explanatory configuration diagram;

FIG. 5 is an oblique diagram showing a head-mounted display;

DETAILED DESCRIPTION OF THE PREFERRED EMBODIMENTS

Figure 1:
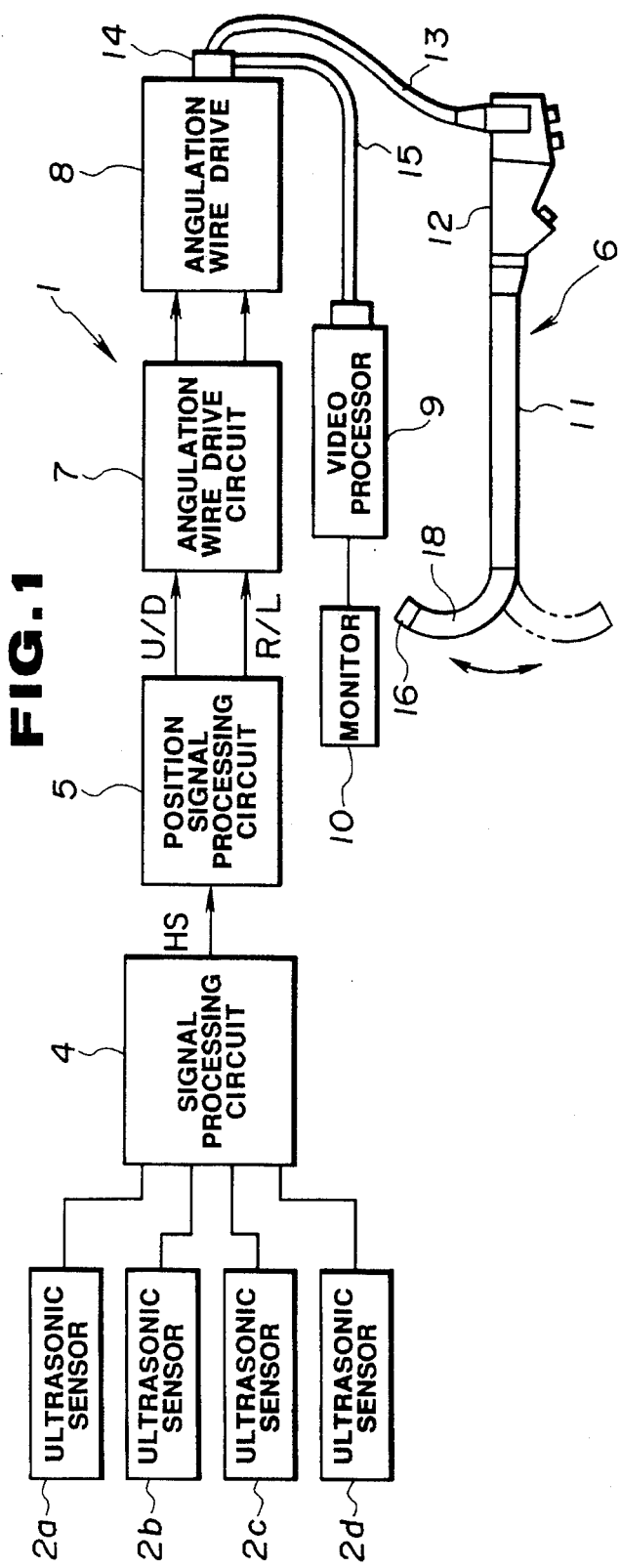
FIGS. 1 and 2 relate to the first embodiment of the present invention.
Figure 2:
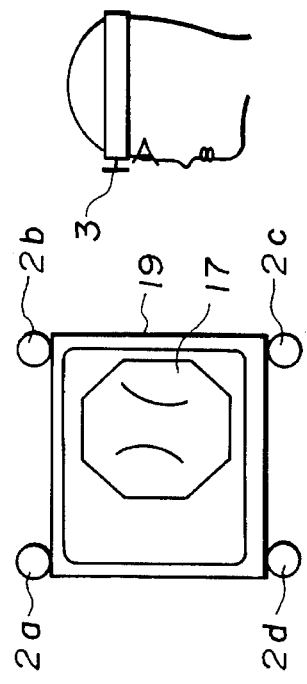

FIGS. 1 and 2 show the first embodiment of the present invention. As shown in FIG. 1, an endoscope system of the first embodiment comprises ultrasonic sensors (four sensors in this embodiment) 2a, 2b, 2c, and 2d serving as movement detecting means for detecting an operator's movement, and an ultrasonic reflecting mirror 3 which is put on an operator's region at which the operator's movement is sensed. Alternatively in this embodiment, the ultrasonic reflecting mirror 3 is placed on the operator's head and reflects ultrasound towards the ultrasonic sensors 2a, 2b, 2c, and 2d, the endoscope system of the first embodiment further comprises a signal processing circuit 4 for inputting the output signals of the ultrasonic sensors 2a, 2b, 2c, and 2d to generate an operator's head position signal HS, and a position signal processing circuit 5 for inputting the head position signal HS to generate a control signal U/D or R/L for controlling a bending section according to the positional state of the operator's head as listed in, for example, Table 1. The endoscope system of the first embodiment further comprises an angulation wire drive circuit 7 for inputting the output signal of the position signal processing circuit 5 to generate a signal for controlling bending of an electronic endoscope 6, an angulation wire drive 8 for driving an angulation wire of the electronic endoscope 6 according to the output signal of the angulation wire drive circuit 7 and thus bending the bending section vertically or laterally, a video processor for processing a signal sent to a light source for supplying illumination light and one from an imaging means, and a monitor 10 for displaying the output video signal of the video processor 9.

TABLE 1

| Positional state of an operator's head | Control of the bending section |
| --- | --- |
| Facing the monitor | Holding it straight |
| Tilting upward | Angling it in U direction (upward) |
| Tilting downward | Angling it in D direction (downward) |
| Orienting rightward | Angling it in R direction (rightward) |
| Orienting leftward | Angling it in L direction (leftward) |

The ultrasonic sensors 2a to 2d are arranged on the right and left tops, and right and left bottoms of the monitor 10 which is opposing an operator as shown in FIG. 2 (or orienting to an operator's face). These sensors 2a to 2d are manufactured by, for example, Murata Mfg. Co., Ltd. of Kyoto, Japan. The ultrasonic sensors 2a to 2d emit ultrasound with wavelengths in different regions, receive ultrasound reflected from the ultrasound reflecting mirror 3, then calculate distances from the reflecting mirror 3. Based on the distances, the signal processing circuit 4 generates a head position signal HS in association with the operator's head position, then outputs the signal to the position signal processing circuit 5.

The electronic endoscope 6 includes an elongated insertion tube 11. An operation unit 12 is coupled to the back end of the insertion tube 11. A cable 13 is extending from the side of the operation unit 12. A connector 14 at the tip of the cable 13 is connected to the angulation wire drive 8. The connector 14 is also connected to the video processor 9 via a cable 15.

An objective, which is not shown, is mounted at a distal end 16 of the insertion tube 11. A CCD or any other solid-state imaging device is arranged on the focal plane of the objective. A signal photoelectrically transferred by the solid-state imaging device enters the video processor 9. After signal processing, an endoscopic image 17 appears on a monitor 10 as shown in FIG. 2.

A bending section 18 is formed adjoining the distal end 16 of the insertion tube. The bending section 18 tenses or relaxes (pulls or pushes) an angulation wire, which is not shown, to bend the bending section 18 upward (U), downward (D), rightward (R) or leftward (L).

Depending on the positional state of an operator's head on which an ultrasound reflecting mirror 3 is put, the position signal processing circuit 5 inputs a control signal U/D or R/L for controlling the bending section to the angulation wire drive circuit 7. The angulation wire drive 8 is driven with a control signal sent from the angulation wire drive circuit 7. The angulation wire drive 8 is formed with, for example, a motor. With the rotation of the motor, the angulation wire is tensed or relaxed to bend the bending section 18 upward, downward, rightward, or leftward. A switching means, which is not shown, is installed to select either an auto mode for automatically bending the bending section by detecting the position of an operator's head or a manual mode in which an operator controls the motor using a bending switch to bend the bending section.

According to the first embodiment, ultrasonic sensors 2a to 2d emit ultrasound with wavelengths in different regions, then an ultrasound reflecting mirror 3, which is put on an operator's head, reflects the ultrasound. The ultrasonic sensors 2a to 2d receive the reflected ultrasound and calculate the distances from the ultrasound reflecting mirror 3. Based on the calculated distances, a signal processing circuit 4 generates a head position signal HS in association with the positional state of the operator's head, then outputs the signal to a position signal processing circuit 5. The position signal processing circuit 5 generates a control signal U/D or R/L for bending a bending section 18 as listed in Table 1 according to the head position signal HS, then outputs the signal to an angulation wire drive circuit 7. The angulation wire drive circuit 7 controls drive of, for example, a motor to bend the bending section 18 upward, downward, rightward, or leftward.

In the aforesaid embodiment, ultrasound is employed to detect an operator's movement. Laser beams may be used on behalf of ultrasound.

FIGS. 3 to 7 show the second embodiment. As shown in FIG. 7, an endoscope system 51 of this embodiment comprises a stereo electronic endoscope 52, a video processor 53, right and left head-mounted displays (hereafter, HMD) 54R and 54L, a data glove 55 (for example, a product of U.S. VPL Inc.) (the same applies hereafter) for detecting the movements of fingers, and a three-dimensional (hereafter, 3D) digitizer 56 (for example, a product of U.S. McDonnel Douglas Corp.) (the same applies hereafter) made up of a magnetic generator 56a for detecting the movement of a hand wearing the data glove 55, and a sensor 56b.

The stereo electronic endoscope 52 includes an elongated insertion tube 61, an operation unit 62, and a cable 63 extending from the operation unit 62. A connector 64 at the tip of the cable 63 can be connected to a video processor 53 so that it can be disconnected freely. When the connector 64 is connected, the light from a light source lamp 65 in the video processor 53 enters the end plane of a light guide 66, comes to the end plane of a distal end 67 of the insertion tube 61, then goes forward from an illumination lens 68.

The distal end 67 is provided with a pair of objectives 69R and 69L. A CCD, which is not shown, is arranged on each of the focal planes of the lenses 69R and 69L. The CCDs perform photoelectric transfer and supply the photoelectrically-transferred signals to a camera control unit (CCU) in the video processor 53.

A bending section 72 is formed adjoining the distal end 67. The bending section 72 is connected to a bending motor (not shown) in the operation unit 62 via a wire which is not shown. The motor is connected to a motor control 73 via a signal line. The motor control 73 controls rotation of the motor according to a control signal sent from a hand movement data processor 74 and thus bends the bending section 72.

Figure 4A:
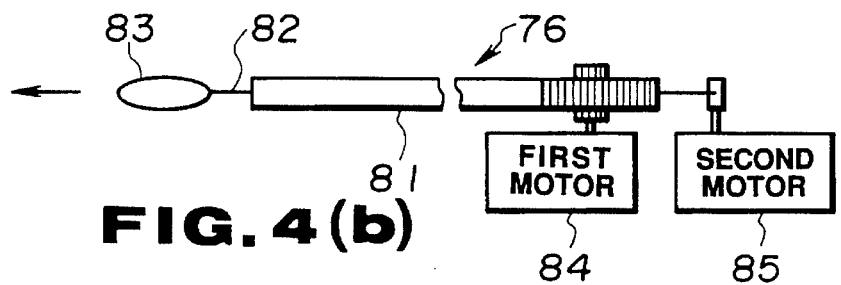
FIGS. 4(a)–4(d) are explanatory diagrams showing control of a diathermic snare.
Figure 4B:

The electronic endoscope 52 has a channel 75 to which a diathermic snare 76 shown in FIG. 4(a), for example, can be inserted. The diathermic snare 76 is made up of an outer casing 81 and a snare wire 82 running through the outer casing 81. A loop 83 is formed at the tip of the snare wire 82. A screw thread is formed on the back end of the outer casing 81, so that a first motor 84 can advance or withdraw the outer casing 81. A second motor 85 is connected to the back end of the snare wire 82, so that the snare wire 82 can advance or withdraw with the rotation of the second motor 84. The first or second motor 84 or 85 is also controlled with a control signal sent from the motor control 73.

Figure 5:
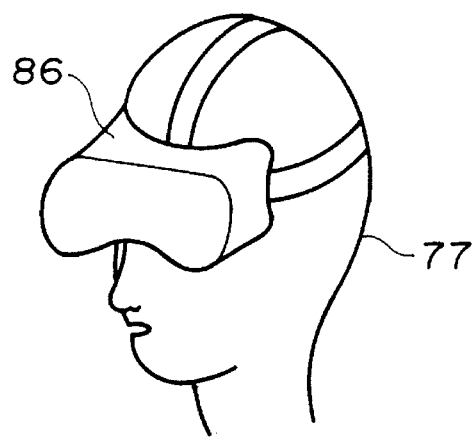

Video signals are acquired by the CCDs, processed by a CCU 71, then fed to the HMDs 54R and 54L. Then, the acquired images are displayed. The HMDs 54R and 54L are stored in a goggle 86 used by an operator 77 which the operator 77 puts on as shown in FIG. 5. When the images displayed on the HMDs 54R and 54L are observed with right and left eyes, the images are seen three-dimensionally.

The data glove 55 accommodates multiple optical fibers 87. Light is supplied from a light emitting circuit 88 to the ends of the optical fibers 87. Light emitted from the other ends of the optical fibers 87 is detected by a light receiving circuit 89. The light attenuation rate of the optical fibers 87 varies depending on the movements of fingers. An amount of light associated with the light attenuation rate is detected by the light receiving circuit 89, then transmitted to an attenuation rate detector 91. VPL (U.S.) products may be employed as the data glove 55 and 3D digitizer 56.

The attenuation rate that the attenuation rate detector 91 detects is supplied to a data processing circuit 92. The data processing circuit 92 accesses the attenuation rate of light attenuated by the optical fibers 87 to detect movements of fingers, creates a computer graphic of a hand according to the detected states of fingers, then outputs the graphic data to the CCU 71. An oscillation circuit 93 supplies oscillation current to a magnetic generator 56a incorporated in the data glove 55, causing the magnetic generator 56a to generate an AC magnetic field. A magnetic sensor 56b detects the AC magnetic field, then outputs the detected signal to the data processing circuit 92 via a detector 94.

Figures 6A, 6B, 6C:
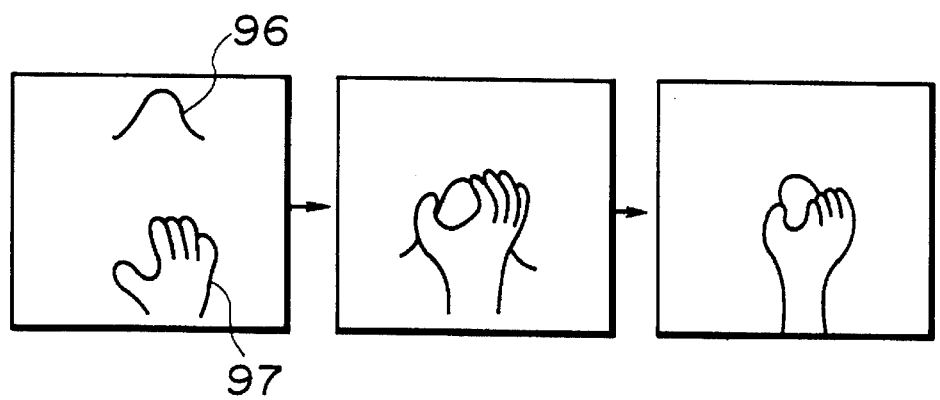
FIGS. 6(a)–6(c) are explanatory diagrams for explaining a synthetic image of an endoscopic image and a computer graphic of a hand.
Figures 7A, 7B, 7C:
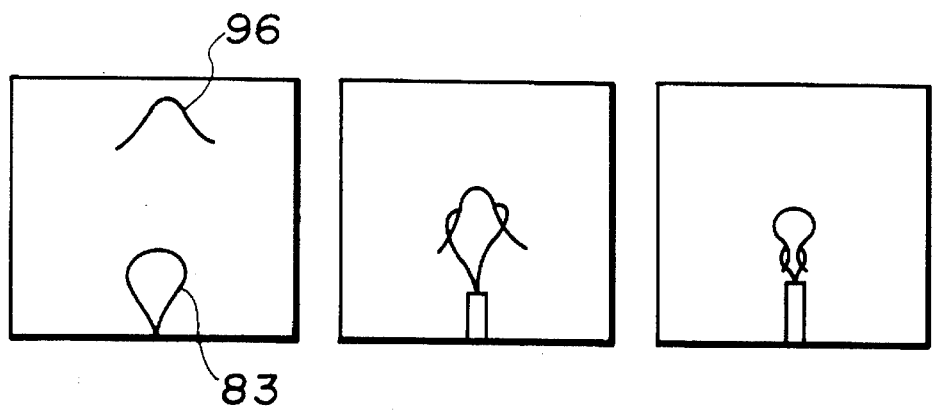
FIGS. 7(a)–7(c) are explanatory diagrams.

The data processing circuit 92 assesses the output of the 3D digitizer made up of the magnetic generator 56a and sensor 56b to detect the position of a hand in the data glove 55. A timing for transmitting a computer graphic of the hand to the CCU 71 according to the detected position is controlled, then the computer graphic of the hand is superimposed on an endoscopic image superimposing a CG image of a hand on an endoscope image by a superimposing means 71S of a CCU 71. FIG. 6(a) shows the superimposition. A polyp 96 is seen in an endoscopic image. When the hand is extended, the computer graphic 97 of the hand is superimposed on the endoscopic image. When the hand is extended, the movement of extending the hand is detected. The first and second motors 84 and 85 are driven according to the movement of the hand as shown in FIG. 4(a) (See FIG. 4(b)). A loop 83 of a diathermic snare 76 projects towards the polyp 96, as shown in FIGS. 7(a)–7(c).

Figure 4C:
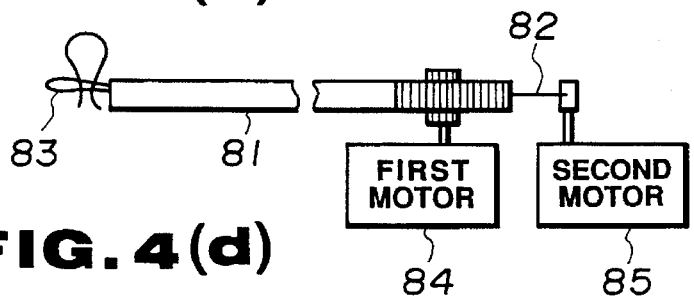
Figure 4D:

When a hand in the state of FIG. 6(a) is extended forward and a polyp 96 is grasped as shown in FIG. 6(b), a diathermic snare 76 is driven accordingly to catch the polyp 96 with the loop 83. When the hand is moved to grasp the polyp 96 as shown in FIG. 6(c), the loop 86 is pulled to resect the polyp. This movement is also shown in FIGS. 4(c) and 4(d). When the hand is closed firmly to grasp the polyp, the second motor 85 is driven to pull a snare wire 82 and eventually resect the polyp 96.

In this embodiment, monitor images in which the movements of a hand are synthesized appear as shown in FIG. 6(a)–6(c). On the other hand, the actual scenes are visualized as shown in FIG. 7(a)–7(c). Therefore, when an operator moves the hand on synthetic (three-dimensional) images shown in FIG. 6, the operator can resect the polyp 96 using the snare as shown in FIG. 7.

Figure 3:
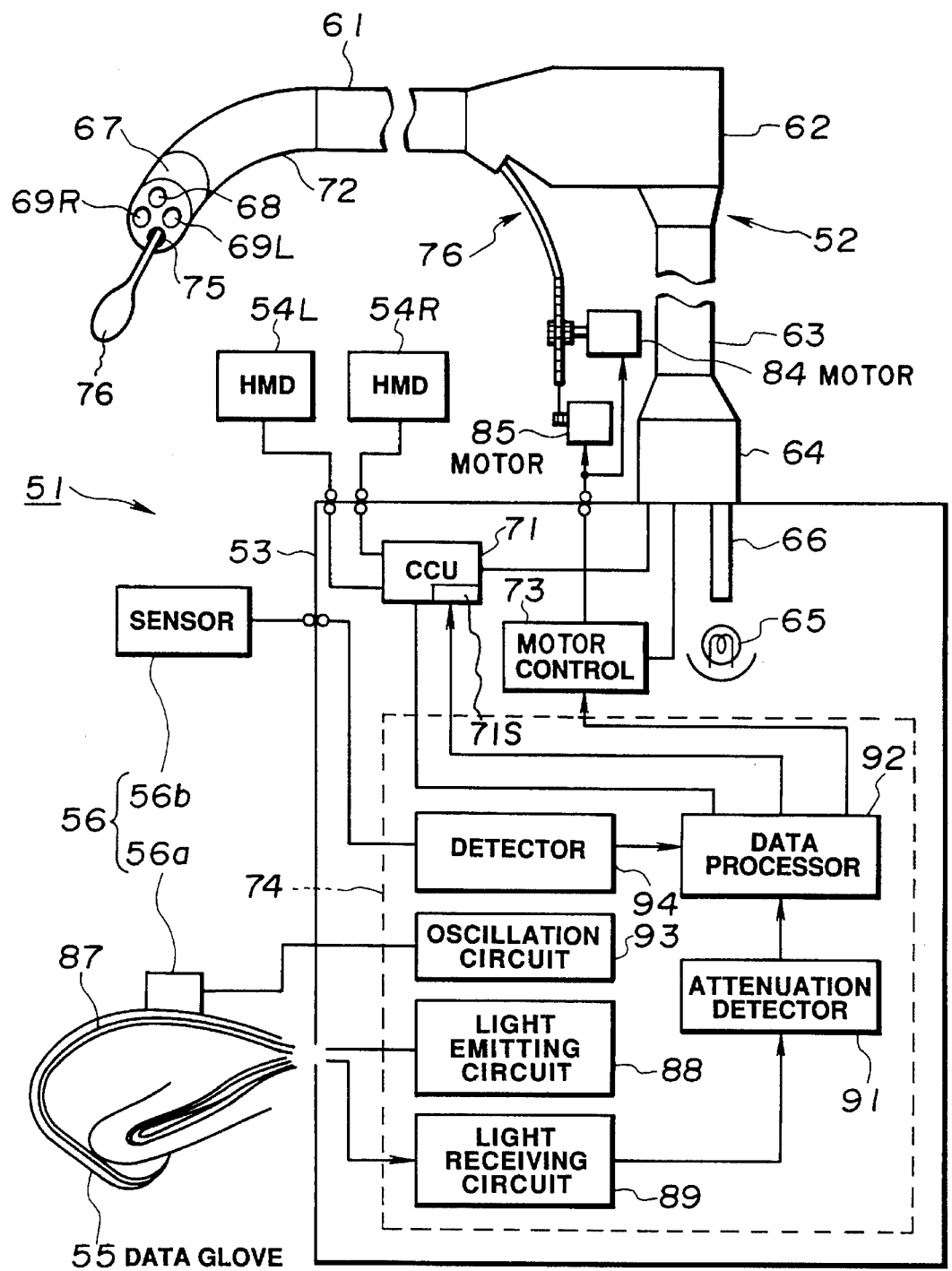

In this embodiment, when synthesized images shown in FIG. 6(a)–6(c) are displayed, the actual images of a treatment adapter are deleted. In FIG. 3, a diathermic snare 76 is running through a channel 75 of an electronic endoscope 52, and the proximal portion is extending outside. However, the proximal portion of the diathermic snare 76 may be incorporated in an operation unit 62. Even in this embodiment, a switching means, which is not shown, is installed. When the switching means is turned off, normal manual operation is enabled.

According to the present invention, it will be apparent that a wide range of different working modes can be formed on the basis of the invention without departing from the spirit and scope of the invention. This invention is not restricted to any specific working modes but limited to the appended claims.

What is claimed is:

1. An endoscope system, comprising:

a medical device for applying medical care to a subject by changing at least a part of a shape of said medical device;

a driving means for actuating said medical device;

a movement detecting means, having at least one sensor for receiving signals from at least one signal source, for processing said received signals, and for detecting a movement of an operator who operates said medical device; and a control means, operably connected to said movement detecting means, for controlling said driving means to actuate said medical device and for changing at least a part of a shape of said medical device according to said operator's movement which is detected by said movement detecting means, wherein said movement detecting means includes a means for detecting a movement of one of an operator's hand and an operator's head, and a superimposing means for superimposing an image associated with the movement of one of the hand and head on an image which an imaging means generates.

2. An endoscope system according to claim 1, wherein said movement detecting means includes a signal processing means for processing detected signals.

3. An endoscope system according to claim 1, wherein said medical device is an endoscope and said driving means is a bending drive for bending a bending section of an endoscope.

4. An endoscope system according to claim 1, wherein said medical device is a treatment adapter adapted to be routed through a treatment adapter channel of an endoscope into a subject's body and said driving means actuates said treatment adapter.

5. An endoscope system according to claim 4, wherein said treatment adapter is a diathermic snare made up of an outer casing and a snare wire which runs through the outer casing and has a loop formed at a tip portion thereof and said driving means advances and withdraws said outer casing and said snare independently.

6. An endoscope system according to claim 1, wherein said at least one sensor of said movement detecting means is an ultrasonic sensor for detecting the positional state of an operator's head and recognizing the operator's movement according to the position of the operator's head.

7. An endoscope system according to claim 1, further comprising an imaging means for generating images of a body of said subject and displaying the images on a monitor.

8. An endoscope system, comprising:

a medical device for applying medical care to a subject;

a driving means for actuating said medical device;

a movement detecting means, having at least one sensor for receiving signals from at least one signal source, for processing said received signals, and for detecting a movement of an operator who operates said medical device;

a control means, operably connected to said movement detecting means, for controlling said driving means to actuate said medical device according to said operator's movement which is detected by said movement detecting means; and an imaging means for generating images of a body of said subject and displaying the images on a monitor, wherein said detecting means includes a means for detecting a movement of an operator's hand and a superimposing means for superimposing an image associated with the movement of the hand on an image which said imaging means generates.

9. An endoscope system, comprising:

a medical device for applying medical care to a subject;

a driving means for actuating said medical device;

a movement detecting means, having at least one sensor for receiving signals from at least one signal source, for processing said received signals, and for detecting a movement of an operator who operates said medical device;

a control means, operably connected to said movement detecting means, for controlling said driving means to actuate said medical device according to said operator's movement which is detected by said movement detecting means; and an imaging means for generating images of a body of said subject and displaying the images on a monitor, wherein said detecting means includes a means for detecting a movement of an operator's hand and a superimposing means for superimposing an image associated with the movement of the hand on an image which said imaging means generates, and wherein said control means drives said driving means to control said medical device so that said medical device operates in association with a movement of a hand.

10. An endoscope system, comprising:

a medical device for applying medical care to a subject;

a driving means for actuating said medical device;

a movement detecting means, having at least one sensor for receiving signals from at least one signal source, for processing said received signals, and for detecting a movement of an operator who operates said medical device;

a control means, operably connected to said movement detecting means, for controlling said driving means to actuate said medical device according to said operator's movement which is detected by said movement detecting means; and an imaging means for generating images of a body of said subject and displaying the images on a monitor, wherein said detecting means includes a means for detecting a movement of an operator's hand and a superimposing means for superimposing an image associated with the movement of the hand on an image which said imaging means generates, and wherein said means for detecting a movement of a hand includes a data glove.

* * * * *